United States Patent
Auderset et al.

(10) Patent No.: US 9,173,722 B2
(45) Date of Patent: Nov. 3, 2015

(54) ANCHOR FOR SECURING A TOOTH REPLACEMENT

(75) Inventors: Adrian Auderset, Nidau (CH); Markus Bluemli, Biel/Bienne (CH); Mathias Strazza, Meinisberg (CH); Daniel Blaser, Lyss (CH); Gary Cooper, Meinisberg (CH); Elmar Mock, Colombier (CH); André Klopfenstein, La Neuveville (CH)

(73) Assignee: CENDRES + METAUX SA, Biel/Bienne (CH)

( * ) Notice: Subject to any disclaimer, the term of this patent is extended or adjusted under 35 U.S.C. 154(b) by 156 days.

(21) Appl. No.: 12/443,420

(22) PCT Filed: Sep. 28, 2007

(86) PCT No.: PCT/CH2007/000481
§ 371 (c)(1),
(2), (4) Date: Mar. 27, 2009

(87) PCT Pub. No.: WO2008/040134
PCT Pub. Date: Apr. 10, 2008

(65) Prior Publication Data
US 2009/0246733 A1    Oct. 1, 2009

(30) Foreign Application Priority Data
Oct. 2, 2006 (CH) ...................... 1563/06

(51) Int. Cl.
*A61C 8/00*    (2006.01)
(52) U.S. Cl.
CPC .............. *A61C 8/005* (2013.01); *A61C 8/0053* (2013.01); *A61C 8/0065* (2013.01); *A61C 8/0089* (2013.01); *A61C 8/0054* (2013.01); *A61C 8/0066* (2013.01); *A61C 8/0069* (2013.01)

(58) Field of Classification Search
CPC ...... A61C 8/005; A61C 8/0018; A61C 8/006; A61C 8/0054; A61C 8/0069
USPC .............. 433/182, 201.1, 193, 181, 172–174; 606/53, 266, 61
See application file for complete search history.

(56) References Cited

U.S. PATENT DOCUMENTS 3,618,212 A * 11/1971 Weissman et al. ............ 433/174
3,732,621 A *  5/1973 Bostrom ....................... 433/174
(Continued)

FOREIGN PATENT DOCUMENTS

EP    288702 A2 * 11/1988 .............. A61C 8/00
EP    0 580 945    2/1994
(Continued)

OTHER PUBLICATIONS

Translation—EP 580945 A1.*
(Continued)

*Primary Examiner* — Cris L Rodriguez
*Assistant Examiner* — Matthew Saunders
(74) *Attorney, Agent, or Firm* — Foley & Lardner LLP

(57) ABSTRACT

An anchor for securing a tooth replacement includes an anchoring part secured to an implant or jaw, having a recess, and a pivoting part to which the tooth replacement can be secured and which contains a pin. The pivoting part is pivotable with respect to the anchoring part when the pin is received in the recess. The anchor is configured to permit application of a hardenable substance in the recess of the anchoring part so as to fix the pivoting part in a defined position of pivoting.

13 Claims, 4 Drawing Sheets

(56) References Cited

U.S. PATENT DOCUMENTS

| | | | |
|---|---|---|---|
| 4,431,416 A * | 2/1984 | Niznick | 433/174 |
| 4,713,004 A * | 12/1987 | Linkow et al. | 433/174 |
| 4,793,808 A * | 12/1988 | Kirsch | 433/173 |
| 4,832,601 A * | 5/1989 | Linden | 433/173 |
| 4,854,872 A * | 8/1989 | Detsch | 433/173 |
| 4,907,969 A * | 3/1990 | Ward | 433/173 |
| 5,071,350 A * | 12/1991 | Niznick | 433/173 |
| 5,073,110 A * | 12/1991 | Barbone et al. | 433/173 |
| 5,116,225 A * | 5/1992 | Riera | 433/173 |
| 5,178,539 A * | 1/1993 | Peltier et al. | 433/173 |
| 5,195,891 A * | 3/1993 | Sulc | 433/173 |
| 5,302,125 A | 4/1994 | Kownacki et al. | |
| 5,417,570 A * | 5/1995 | Zuest et al. | 433/177 |
| 5,890,902 A * | 4/1999 | Sapian | 433/173 |
| 6,030,219 A * | 2/2000 | Zuest et al. | 433/181 |
| 6,287,115 B1 * | 9/2001 | Lustig et al. | 433/173 |
| 6,287,117 B1 * | 9/2001 | Niznick | 433/173 |
| 6,299,447 B1 * | 10/2001 | Zuest et al. | 433/172 |
| 6,500,003 B2 * | 12/2002 | Nichinonni | 433/173 |
| 6,695,616 B2 * | 2/2004 | Ellison | 433/174 |
| 6,786,725 B2 * | 9/2004 | Lustig et al. | 433/173 |
| 6,843,653 B2 * | 1/2005 | Carlton | 433/174 |
| 7,214,063 B2 * | 5/2007 | Cohen | 433/174 |
| 7,704,076 B2 * | 4/2010 | Mullaly et al. | 433/174 |
| 2005/0042573 A1 * | 2/2005 | Lustig et al. | 433/173 |
| 2005/0181331 A1 * | 8/2005 | Lustig et al. | 433/173 |
| 2005/0192571 A1 * | 9/2005 | Abdelgany | 606/61 |
| 2005/0192572 A1 * | 9/2005 | Abdelgany et al. | 606/61 |
| 2005/0192573 A1 * | 9/2005 | Abdelgany et al. | 606/61 |
| 2006/0046229 A1 * | 3/2006 | Teich | 433/173 |
| 2006/0166168 A1 | 7/2006 | Tinti | |
| 2006/0235385 A1 * | 10/2006 | Whipple | 606/61 |
| 2007/0093832 A1 * | 4/2007 | Abdelgany | 606/61 |
| 2007/0213721 A1 * | 9/2007 | Markworth et al. | 606/61 |
| 2008/0153063 A1 * | 6/2008 | Mullaly et al. | 433/174 |

FOREIGN PATENT DOCUMENTS

| | | | |
|---|---|---|---|
| EP | 580945 A1 * | 2/1994 | A61C 8/00 |
| EP | 1 201 200 | 5/2002 | |
| JP | A-46-004095 | 11/1971 | |
| JP | A-2005-270529 | 10/2005 | |
| JP | A-2007-504875 | 3/2007 | |

OTHER PUBLICATIONS

Office Action issued in corresponding JP Application No. 2009-530746 with partial English translation, Dated Jun. 15, 2012, 4 pages.

* cited by examiner

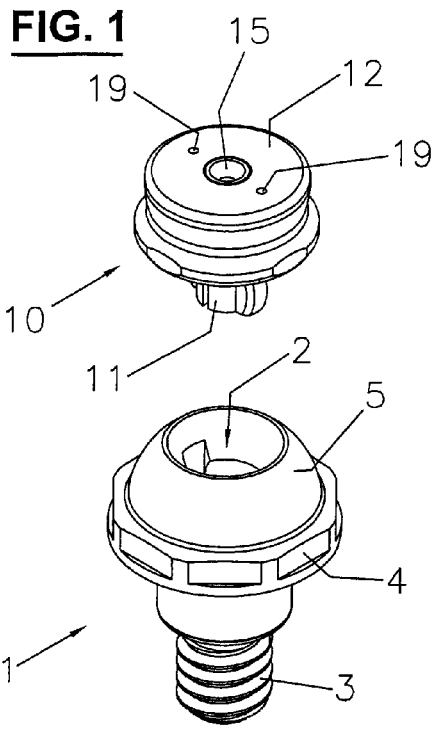
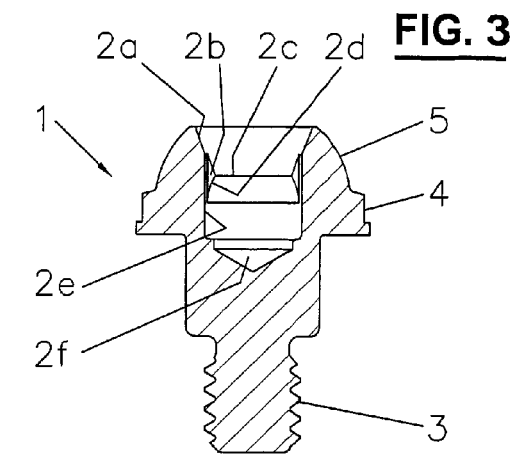
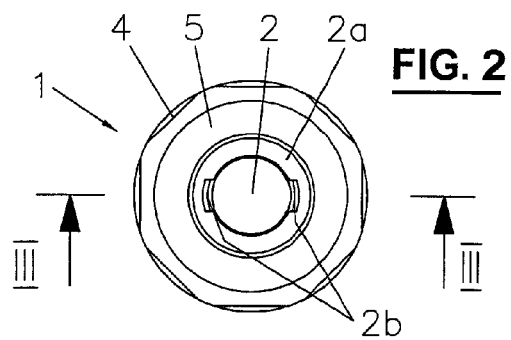
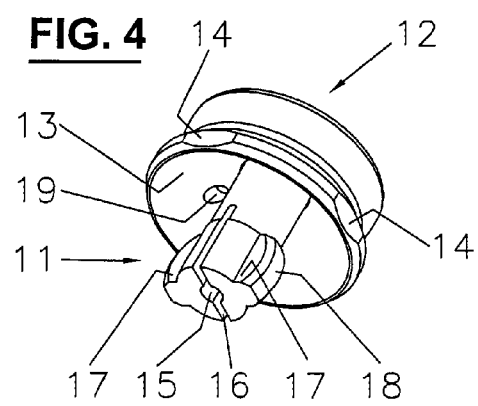
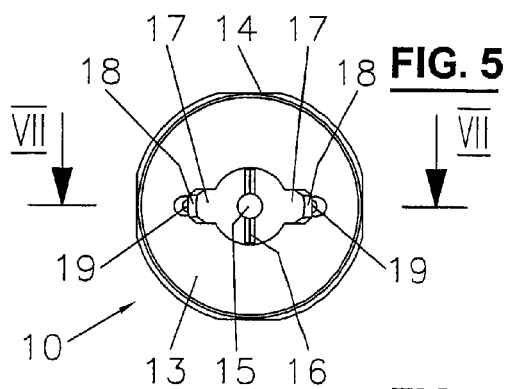
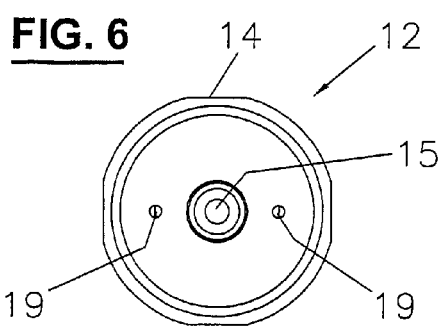
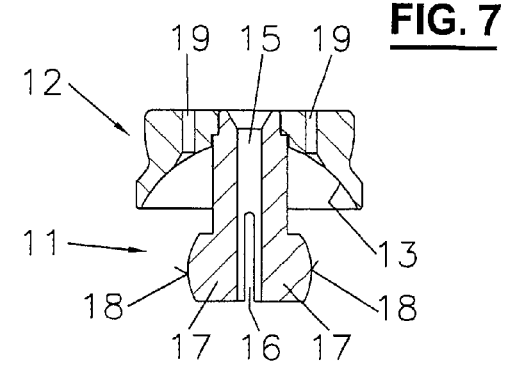

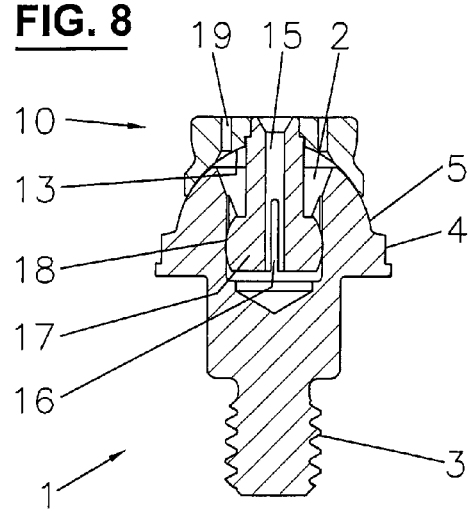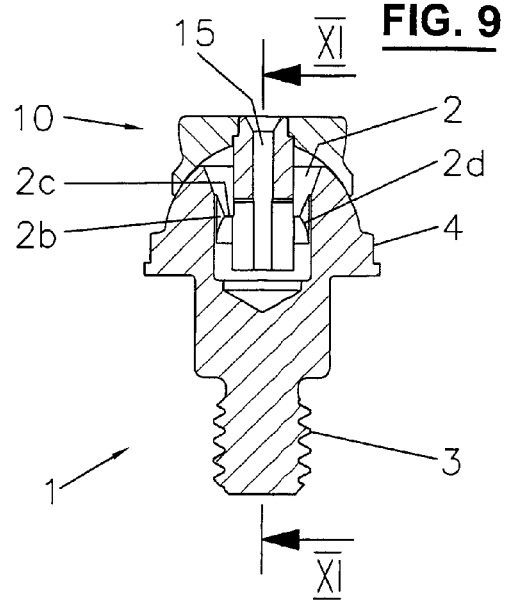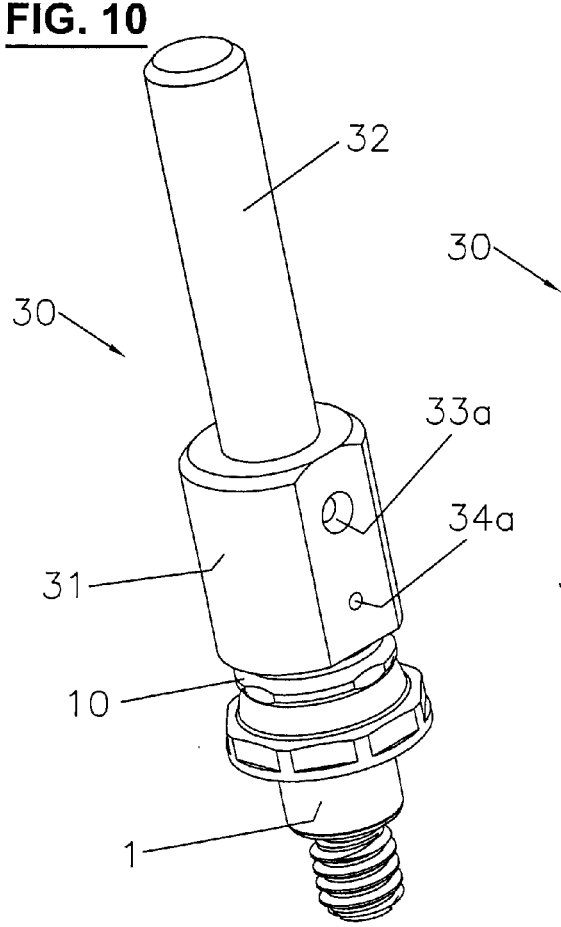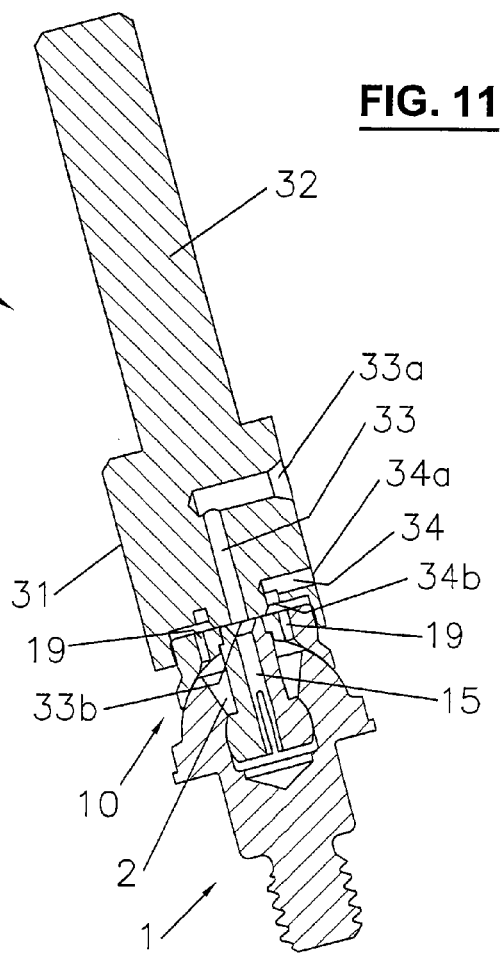

FIG. 14
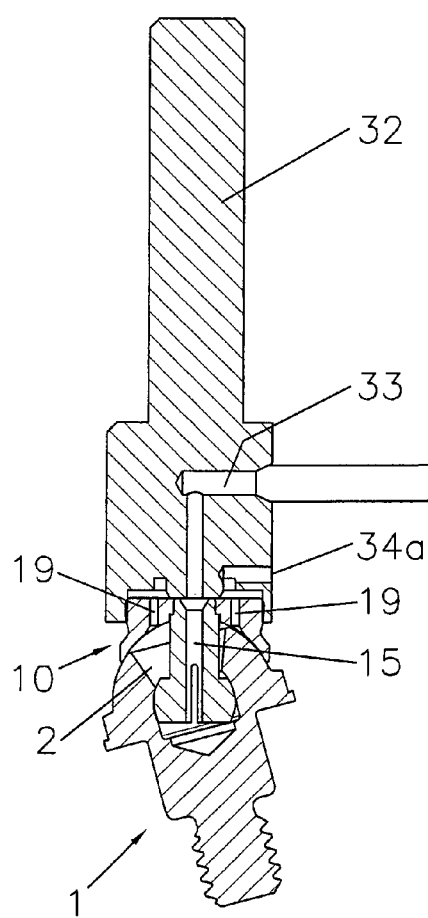
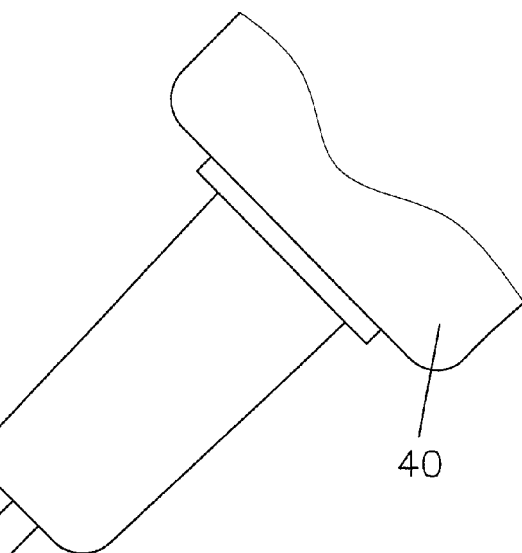
FIG. 15
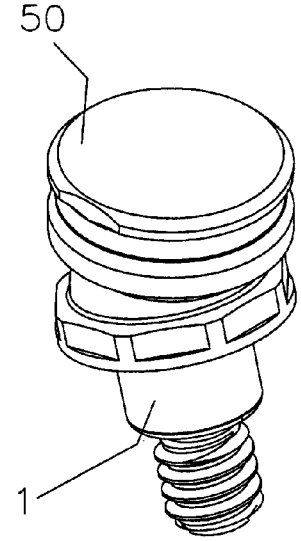
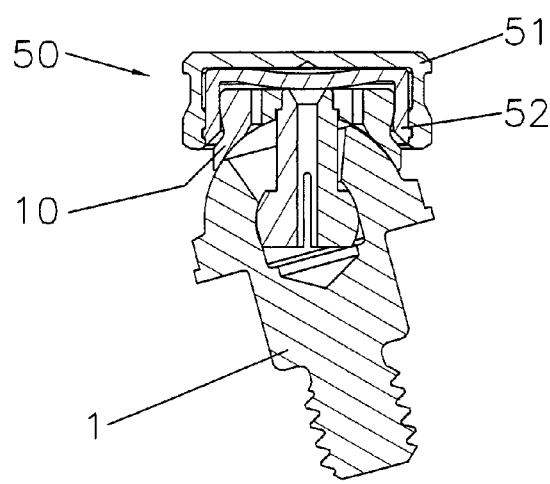
FIG. 16

ANCHOR FOR SECURING A TOOTH REPLACEMENT

This application is the National Phase of PCT/CH2007/000481, filed Sep. 28, 2007, which claims priority to Swiss Application No. 01563/06, filed Oct. 2, 2006. The contents of the foregoing applications are incorporated by reference in their entirety.

BACKGROUND (a) Field of Embodiments

The present invention relates to an anchor for securing a tooth replacement according to the preamble of claim 1.

(b) Description of Related Art

Anchors for securing a tooth replacement on implants can often not be fitted in the mouth in the ideal direction, for example owing to the bone conditions. If, for example, a dental prosthesis is to be secured by means of the anchor, the longitudinal direction of the anchor may deviate from the direction of insertion of the dental prosthesis. This angular deviation is also referred to as divergence.

It is known from patent specification U.S. Pat. No. 3,732,621 to provide the anchoring part with a pivoting part. As a result, it is possible, after fitting the anchoring part, to orient the pivoting part accurately and to compensate for any divergence. Mechanical securing means are provided in order to secure the pivoting part in a specific pivoting position. Such means have, inter alia, the disadvantage that the structure of the anchor is relatively complicated. There is also the risk that the pivoting part will come away from the adjusted pivoting position and that the tooth replacement will no longer be held securely.

On the basis of this prior art, an object of the present invention is so to develop the known anchor that it has a more simplified structure.

SUMMARY

An anchor which achieves this object is indicated in claim 1. The other claims indicate preferred embodiments and an auxiliary instrument. The anchor according to the invention comprises means for applying a hardenable substance in the recess of the anchoring part. As a result, the pivoting part can be fixed securely in a specific pivoting position with a relatively simple structure.

BRIEF DESCRIPTION OF DRAWINGS

The invention will be explained hereinafter by means of a preferred embodiment with reference to Figures.

FIG. 1 is a perspective view of the anchor according to the invention before assembly;

FIG. 2 is a plan view of the anchoring part of the anchor according to FIG. 1;

FIG. 3 shows the anchoring part in a section according to the line III-III in FIG. 2;

FIG. 4 is a perspective view of the pivoting part of the anchor according to FIG. 1;

FIG. 5 is a bottom view of the pivoting part according to FIG. 4;

FIG. 6 is a plan view of the pivoting part according to FIG. 4;

FIG. 7 shows the pivoting part in a section according to the line VII-VII in FIG. 5;

FIG. 8 shows the assembled anchor according to FIG. 1, the anchoring part being sectioned in accordance with the line III-III in FIG. 2 and the pivoting part according to the line VII-VII in FIG. 5;

FIG. 9 shows the anchor according to FIG. 8 after the pivoting part has been rotated through 90 degrees;

FIG. 10 is a perspective view of an arrangement with the anchor according to FIG. 9 and an auxiliary instrument placed thereon;

FIG. 11 shows the arrangement according to FIG. 10 sectioned according to the line XI-XI in FIG. 12, the sectional plane XI-XI in which the anchor is sectioned likewise being indicated in FIG. 9;

FIG. 14 is a partially sectioned detailed view of the arrangement according to FIG. 13;

FIG. 15 shows the anchor according to FIG. 14 together with a female part placed thereon; and FIG. 16 shows a section through FIG. 15 in the same sectional plane as FIG. 14.

DETAILED DESCRIPTION

Figure 12:
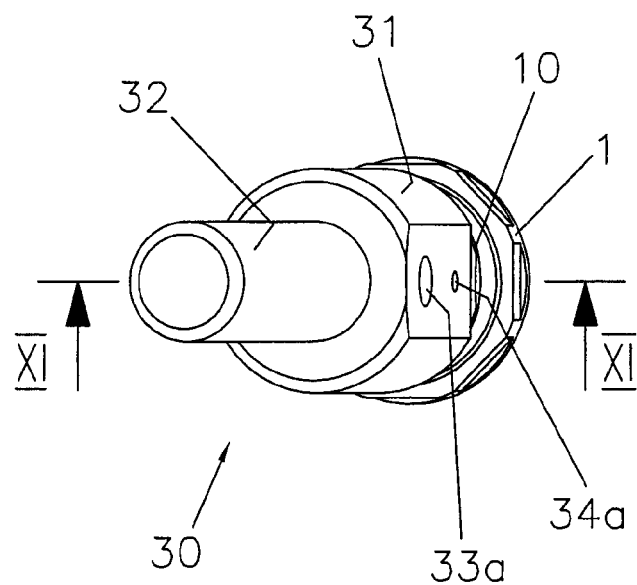
FIG. 12 is a plan view of the arrangement according to FIG. 10.
Figure 13:
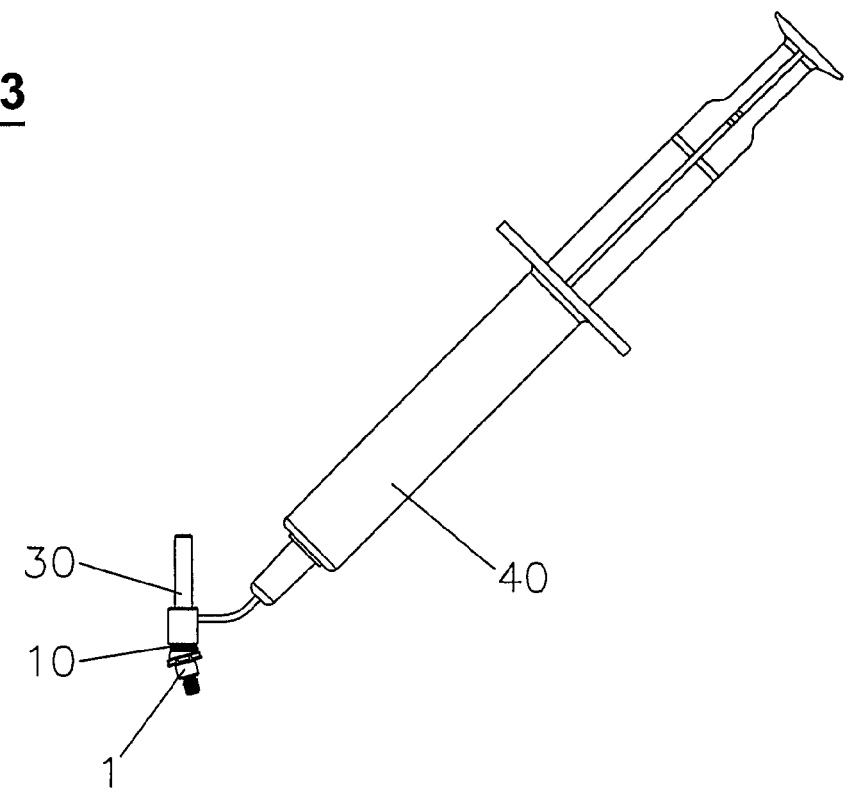
FIG. 13 shows the arrangement according to FIG. 10 together with a filling syringe after the pivoting part has been pivoted.

The anchor shown in FIG. 1 comprises an anchoring part 1 which can be fixed to an implant (not shown), and a pivoting part 10 to which a tooth replacement (not shown), for example a dental prosthesis, can be secured. The pivoting part 10 contains a pin 11 which can be accommodated in a recess 2 in the anchoring part 1.

The anchoring part 1 comprises a pin 3 having a thread, and an anchoring head having an edge which is in the form of a polyhedron 4 and which can be brought into engagement with a suitable tool in order to be able to screw the anchoring part 1 into an implant and tighten it.

As also shown in FIGS. 2 and 3, the anchoring head has a spherical outer face 5 in which the recess 2 has been formed. The recess 2 is delimited by a stop face 2a which tapers towards the base end of the anchoring part 1 and which is bordered by a spherical inner face 2d which merges into a cylindrical inner face 2e.

The stop face 2a is in a conical form but it may also be in a different form. The stop face 2a defines the maximum pivoting angle through which the pivoting part 10 can be pivoted relative to the longitudinal axis of the anchoring part 1. In the present example, this maximum pivoting angle is 20 degrees. Depending on the intended purpose, the stop face 2a may be in a different form, the maximum pivoting angle preferably lying in the range of from 10 degrees to 30 degrees.

In the example shown here, the base end 2f of the recess 2 is delimited by a conical face owing to the manner in which the anchoring part 1 was manufactured. The end 2f may, however, be in any desired form.

The transition between the stop face 2a and the spherical inner face 2d forms a neck 2c which prevents the pivoting part 10 from falling out when the pin 11 of the pivoting part 10 engages in the recess 2. The neck 2c has a respective opening 2b at each of two opposite sites. The openings 2b enable the end of the pin 11 to be inserted into the inner space of the recess 2 delimited by the neck 2c.

The configuration of the pivoting part 10 can be seen more exactly in FIGS. 4 to 7. The pivoting part 10 comprises a pivoting head 12 in the middle of which the pin 11 is fitted. The underside of the pivoting head 12 is formed by a spherical face 13 which, after mounting, rests on the outer face 5 of the anchoring part 1 and thus acts as a ball socket. The face 13 is in a concave form. The upper side of the pivoting head 12 is matched to the desired type of connection to the tooth replacement. In the present case, the pivoting head 12 is in a form such that the tooth replacement can be releasably secured thereto by means of a female part. The pivoting head 12 has sites 14 which are flattened at the lateral edge. As a result, the pivoting part 10 can be connected in a rotationally secure manner to a suitable mounting instrument and fitted to the anchoring part 1.

The pivoting part 10 can also be mounted on the anchoring part 1 by means of a mounting instrument in the form of pliers having two pins which can be inserted into the bores 19 in the pivoting head 12. If this type of mounting is preferred, the flattened sites 14 on the pivoting head 12 may be omitted.

The pin 11 has a through-bore 15 so that an internal duct is formed from an inlet aperture in the pivoting head 12 as far as the end of the pin 11. A securing means in the form of a hardenable substance can be introduced through this internal duct 15 and into the recess 2 from outside, and the pivoting part 10 can thus be fixed in the desired pivoting position on the anchoring part 1. The end of the pin 11 is provided with a slot 16 and two opposing projections in the form of wings 17. The outer sides of the wings 17 comprise spherical faces 18 and, after mounting, co-operate with the spherical inner face 2d of the anchoring part 1. The pivoting head 12 is provided with through-bores 19 which are used as internal ducts for ventilation and also to monitor whether sufficient securing means has been introduced to fix the pivoting part 10 in position.

The anchor is fitted in the mouth by screwing the anchoring part 1 into the implant and then inserting the pivoting part 10. For this purpose, the pivoting part 10 is so oriented in relation to the anchoring part 1 that the wings 17 come to rest in the openings 2b and can be passed over the neck 2c and into the inner space of the recess 2 (see FIG. 8). Before the pivoting part 10 is brought into the desired pivoting position, it is first rotated about the longitudinal axis of the pin 11 through a specific angle, for example 90 degrees (see FIG. 9). This preliminary rotation reduces the risk that, when the pivoting position is adjusted, the wings 17 will inadvertently come to rest in the openings 2b again and the pivoting part 10 might possibly be lifted from the anchoring part, so that the face 13 no longer rests on the spherical face 5.

Owing to the provision of the slot 16, the end of the pin 11 is in a resilient form, so that the wings 17 can be pressed together and readily inserted into the inner space of the recess 2 delimited by the neck 2c. The maximum diameter of the end of the pin 11 is selected to be slightly greater than the diameter of the sphere on which the inner face 2d lies. The wings 17 thus press against the wall of the recess 2 and therefore generate a pretensioning with the effect that the pivoting part 10 is not fitted in a completely loose manner on the anchoring part 1. This ensures that the pivoting position of the pivoting part 10 changes only when a specific force is exerted thereon in order to pivot it.

Once the pivoting part 10 is located in the desired pivoting position, a securing means is introduced through the internal duct 15 and into the recess 2. Suitable securing means are common hardenable substances, for example substances based on polymers, especially a polymerizate, common filling materials, especially those having a metallic or ceramic core structure, or those on a polymer basis, adhesives, etc. The introduction is stopped when the securing means comes out of the apertures of the bores 19. When the securing means has hardened, the pivoting part 10 has been fixed securely in its pivoting position.

Owing to the provision of a pivoting part 10 having a pin 11 which engages in the recess 2 in the anchoring part 1, a compact joint can be formed which has, in particular, a low structure. In the present example, the joint has three degrees of freedom. The face 13 of the underside of the pivoting part 10 and the outer face 5 of the anchoring part 1 are located substantially on a sphere having a radius R and the inner face 2d of the anchoring part 1 and the faces 18 of the wings 17 are located substantially on a sphere having a radius r, the two spheres having the same centre and r being smaller than R.

As can be seen from FIGS. 8, 9 and 14, the underside 13 of the pivoting head 12 is constructed to protrude sufficiently for the pivoting head 12 to cover the recess 2 even when the pivoting part 10 has been pivoted to the maximum extent.

The anchoring part 1 and the pivoting part 10 are produced from a biocompatible material, for example metal, such as titanium, ceramic material, plastics material or another material which can be used in the dental field. The anchoring part 1 and the pivoting part 10 each form a part which is manufactured from one piece or is assembled from several pieces.

If necessary, the adhesion face of the anchoring part 1 and/or of the pivoting part 10, which face comes into contact with the securing means, is conditioned to bring about an intimate connection of the adhesion face to the securing means. Conditioning can be achieved, for example, by sandblasting the adhesion face or by another type of surface treatment.

In order to facilitate the mounting of the pivoting part 10, an auxiliary instrument 30, which is shown in FIGS. 10 to 12, is optionally provided. The auxiliary instrument 30 comprises an introduction head 31 which can be placed on the pivoting part 10 and connected thereto, and a straight end 32 which is used for optical orientation. The end 32 is selected to be sufficiently long for the overall length of the auxiliary instrument to be longer than the length of the anchoring part 1. The end 32 is in a cylindrical and rigid form and can if necessary be so configured that it is suitable as an insert in a parallelometer.

The introduction head 31 is provided laterally with an inlet aperture 33a and, on the underside, with an outlet aperture 33b. The inlet and outlet apertures 33a, 33b are in fluid communication with each other via an introduction duct 33. The introduction head 31 comprises next to the inlet aperture 33a a ventilation aperture 34a which is in fluid communication with an aperture 34b on the underside of the introduction head 31 via a ventilation duct 34. The underside of the introduction head 31 is in a stepped form so that, when the auxiliary instrument 30 has been placed on the pivoting part 10, the inlet aperture 33a is connected to the internal duct 15 and the two internal ducts 19 of the pivoting part 10 are connected to the aperture 34b of the introduction head 30. The edge of the introduction head 31 is in a form such that it can be releasably connected to the pivoting part 10, for example by forming a snap connection.

In order to orient the pivoting part 10, the auxiliary instrument 30 is placed thereon and is pivoted until the end 32 points in the desired direction for compensating for any divergence. This direction corresponds to the direction of insertion when a removable dental prosthesis is to be fitted to the anchor. An application aid, for example a filling syringe 40 containing the securing means, is then placed on the inlet aperture 33a, and the securing means is introduced until it reaches the internal duct 15 via the introduction duct 33 and finally exits from the ventilation aperture 34a. The auxiliary instrument 30 is constructed in one piece and is manufactured, for example, from plastics material and/or metal.

Optionally, the auxiliary instrument 30 may be used purely to orient the pivoting part 10. In that case, the duct 33 with the apertures 33a and 33b and the duct 34 with the apertures 34a and 34b do not have to be provided. In order to mount the pivoting part 10, first the securing means is introduced through the internal duct 15 and into the recess 2. The head 31 of the auxiliary instrument 30 is then placed on the pivoting part 10 and the latter is brought into the desired pivoting position.

In the embodiment shown here, the anchoring part 1 and the pivoting part 10 form a male part to which the tooth replacement can be secured by means of a female part. FIGS. 15 and 16 show an anchor with a female part 50 placed thereon. The latter comprises a female-part housing 51, and an insert 52. The female part 50 and the male part 1, 10 are in a form such that they are fixed to each other by means of a snap connection.

The female part 50, or female parts 50 when several anchors are present, is (are) secured firmly to the tooth replacement, for example a dental prosthesis, by common methods, such as polymerization. The dentist can also carry out this operation directly on the patient by fitting the female parts to the male parts fixed in the mouth, grinding out the cavity necessary for the female parts in the dental prosthesis and finally securing the latter by means of a polymerizate or other known processing methods. An especially simple securing method results when the dental prosthesis is provided with suitable apertures so that the polymerizate can be introduced directly between the fitted prosthesis and the female parts via the apertures.

The female part 50 and the upper side of the pivoting part 10 do not necessarily have to be in the form shown in FIGS. 15 and 16 but may be adapted to the desired purpose. It is also possible to construct the pivoting part 10 in such a manner that a prosthesis can be fitted tightly thereto and/or an artificial tooth can be fitted thereto.

From the above description, numerous modifications are available to the person skilled in the art without departing from the scope of the invention defined by the claims.

For example, the anchoring part 1 shown here is screwed into a depression in the implant and thus forms an implant structure. The anchoring part can, however, be adapted in accordance with the intended purpose. Thus, for example, it is possible to configure the anchoring part 1 as an implant which can be fitted directly in the jawbone.

In order to be able to introduce the hardenable substance into the recess 2 from outside, it is also possible to provide the anchoring part 1 with an internal duct of the same type as the internal duct 15.

Instead of internal ducts, other means are also possible for applying the hardenable substance in the recess 2. For example, the means may comprise a substance which is located in the recess 2 of the anchoring part 1 and which can be activated in order to form the hardenable substance. A suitable activatable substance is, for example, a solder or a plastics material which is integrated in the recess 2 and which can be activated by heating. On activation, the substance passes into the fluid phase. The pivoting part 10 can then be brought into the desired position and, when the substance has cooled, it has been fixed in position.

The activatable substance may also be in the form of two or more components which are first accommodated separately from each other in the recess 2 and then activated by subsequent mixing so that a hardenable substance is formed. The mixing can be effected, for example, by inserting the pivoting part 10 into the anchoring part 1 and subsequently rotating.

The invention claimed is:

1. An anchor for securing a tooth replacement, comprising: an anchoring part configured to be secured to an implant or jaw and that includes a recess having a curved outer surface, the recess being configured to receive a hardenable substance;
a pivoting part, that includes a pivoting head in a fixed relation to a pin, the pivoting part having a curved underside surface and being configured to secure to the tooth replacement and to be pivotable relative to the anchoring part when the pin is received in the recess, wherein the pivoting part is fastenable in a pivoting position; and
wherein the anchoring part has a first longitudinal axis and a first maximum width seen transversally to said first longitudinal axis and the pivoting part has a second longitudinal axis and a second maximum width seen transversally to said second longitudinal axis, the first maximum width being greater than the second maximum width,
wherein the curved outer surface of the recess and the curved underside surface of the pivoting head contact each other when the pin is received in the recess.

2. The anchor of claim 1, further comprising at least one internal duct through which the hardenable substance can be introduced into the recess of the anchoring part from outside and that is formed in the pivoting part or the anchoring part.

3. The anchor of claim 2, wherein the the hardenable substance can be applied in the recess when the anchoring part and the pivoting part are arranged in a mouth, whereby the pivoting part is fastened in a pivoting position.

4. The anchor of claim 1, wherein the recess comprises a neck, and wherein the neck includes at least one opening through which an end of the pin can be inserted.

5. The anchor of claim 1, wherein the pivoting part comprises a pretensioning mechanism configured to cause the end of the pin to press against a wall of the recess when the pivoting part has been fitted to the anchoring part.

6. The anchor of claim 1, wherein the end of the pin is slotted.

7. The anchor of claim 1, further comprising at least one ventilation duct, wherein the at least one ventilation duct leads into the recess and wherein the at least one ventilation duct is formed in the pivoting part.

8. The anchor of claim 1, further comprising an activatable substance.

9. The anchor of claim 1, wherein, in order to form a pivot joint between the anchoring part and the pivoting part,
an upper side of the anchoring part comprises a first spherical face, the recess is delimited by a second spherical face, the underside of the pivoting part comprises a first spherical counter-face, and the pin comprises at least a second spherical counter-face, and wherein
when the pivoting part has been fitted to the anchoring part, the first counter-face is in contact with the first face and the second counter-face is in contact with the second face.

10. The anchor of claim 1, further comprising a female part used for the releasable securing of the tooth replacement to the pivoting part, wherein the female part and the pivoting part can he connected by a snap connection.

11. The anchor of claim 1, wherein the end of the pin comprises two wings.

12. The anchor of claim 1, further comprising a female part used for the releasable securing of the tooth replacement to the pivoting part, wherein the female part comprises an insert of plastic material or metal.

13. The anchor of claim 1,
wherein the anchoring part further includes an anchoring part outer surface arranged outside of the recess,
wherein the pivoting part includes a pivoting part underside surface, and
wherein the pivoting part underside surface contacts the anchoring part outer surface, when the pin is received in the recess.

* * * * *